(12) United States Patent
Zhang et al.

(10) Patent No.: US 8,379,213 B2
(45) Date of Patent: Feb. 19, 2013

(54) ANALYTIC DEVICE WITH 2D SCANNING MIRROR READER

(75) Inventors: Nan Zhang, Cupertino, CA (US); Pingyi Yan, SheKou ShenZhen (CN)

(73) Assignee: Micropoint Bioscience, Inc., Santa Clara, CA (US)

( * ) Notice: Subject to any disclaimer, the term of this patent is extended or adjusted under 35 U.S.C. 154(b) by 353 days.

(21) Appl. No.: 12/806,735

(22) Filed: Aug. 18, 2010

(65) Prior Publication Data
US 2011/0085171 A1      Apr. 14, 2011

Related U.S. Application Data

(60) Provisional application No. 61/274,857, filed on Aug. 21, 2009.

(51) Int. Cl.
*G01N 21/55* (2006.01)
(52) U.S. Cl. ....................................................... 356/445
(58) Field of Classification Search .................. 356/445
See application file for complete search history.

(56) References Cited

U.S. PATENT DOCUMENTS

| | | | | |
|---|---|---|---|---|
| 4,973,159 | A * | 11/1990 | Sohma et al. | 356/328 |
| 5,486,688 | A | 1/1996 | Iima et al. | |
| 5,914,796 | A | 6/1999 | Selin | |
| 6,122,394 | A | 9/2000 | Neukermans et al. | |
| 6,423,956 | B1 * | 7/2002 | Mandella et al. | 250/201.3 |
| 6,657,758 | B1 | 12/2003 | Garner | |
| 6,710,316 | B2 * | 3/2004 | Mandella et al. | 250/201.3 |
| 6,713,742 | B2 * | 3/2004 | Mandella et al. | 250/201.3 |
| 7,079,301 | B2 | 7/2006 | Monroe et al. | |
| 7,224,507 | B2 * | 5/2007 | Kamiya et al. | 359/290 |
| 7,256,926 | B2 * | 8/2007 | Kamiya et al. | 359/290 |
| 7,307,774 | B1 | 12/2007 | Schnitzer et al. | |
| 7,345,802 | B2 * | 3/2008 | Pezeshki et al. | 359/223.1 |
| 7,426,066 | B2 | 9/2008 | Fu et al. | |
| 7,463,396 | B2 | 12/2008 | Lauer | |
| 7,483,194 | B2 | 1/2009 | Hayakawa et al. | |
| 7,576,862 | B2 * | 8/2009 | Cromwell et al. | 356/445 |
| 7,812,956 | B2 * | 10/2010 | Cromwell et al. | 356/445 |
| 2002/0131139 | A1 * | 9/2002 | Mandella et al. | 359/215 |

FOREIGN PATENT DOCUMENTS

WO      WO 2007/000293      1/2007

OTHER PUBLICATIONS

International Search Report and Written Opinion for PCT/US2010/002286, Apr. 27, 2011.
Piyawattanametha et al (2003) "A surface and bulk micromachined angular vertical combdrive for scanning micromirrors." Optical Fiber Communications Conference, 2003. OFC 2003.

* cited by examiner

*Primary Examiner* — Roy M Punnoose
(74) *Attorney, Agent, or Firm* — Gary Baker; Quine Intellectual Property Law Group, P.C.

(57) ABSTRACT

This invention provides methods of array reading and readers of assay result arrays wherein light can be scanned onto analytical region array members from a light source and/or light can be scanned from array members to a detector. One or more mirrors can have one of more pivotable axes enabling scanning light paths to be established between assay result arrays and other components of an analytical device.

35 Claims, 13 Drawing Sheets

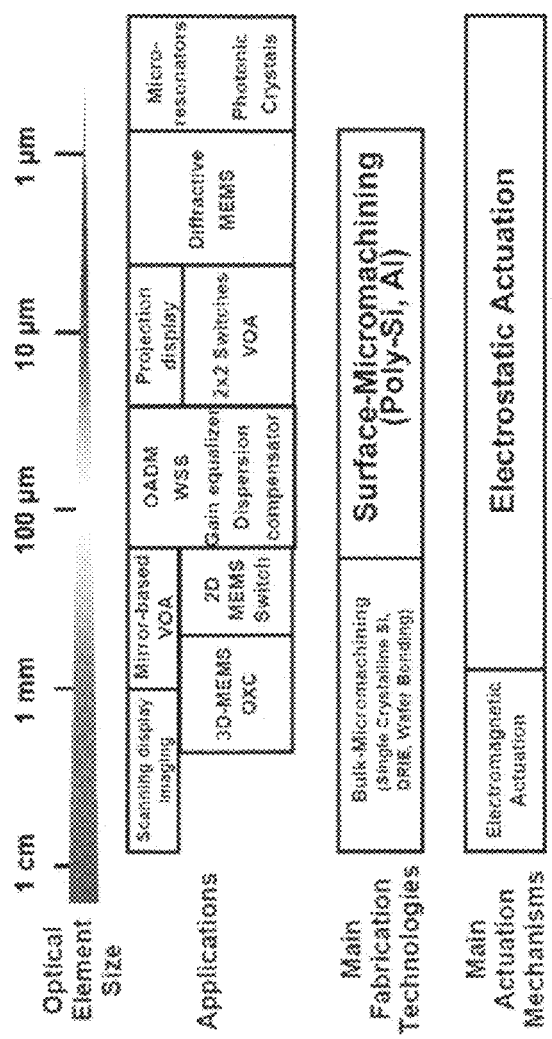
Fig. 9
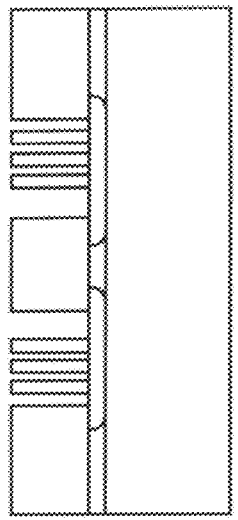
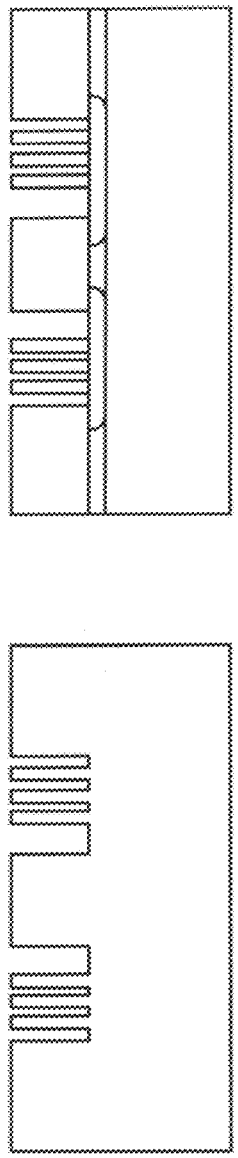
Fig. 10

Optical Path Length: $L = 2b = \dfrac{2\pi w_0^2}{\lambda}$ $\Delta\theta$ : Mechanical Scan Angle $R = aw_0$ : Mirror Radius ($a \sim 2$)

$w_0$ : Beam Waist

ANALYTIC DEVICE WITH 2D SCANNING MIRROR READER

CROSS REFERENCE TO RELATED APPLICATIONS

This application claims priority to and benefit of a prior U.S. Provisional Application No. 61/274,857, Analytic Device with 2D Scanning Mirror Reader, by Nan Zhang, et al., filed Aug. 21, 2009. The full disclosure of the prior application is incorporated herein by reference.

FIELD OF THE INVENTION

The present inventions relate to methods and apparatus to read results from an analytical array by scanning the array with one or more mirrors pivotable about one or more pivot axes. Light from a two-dimensional (2D) array of analytical regions, e.g., on an assay cartridge, is sequentially reflected to or from individual array member regions onto a light detector to read an assay result.

BACKGROUND OF THE INVENTION

Analytical cartridge readers are typically stand alone or desk top devices have many complicated moving parts to read more than one result from the same cartridge. A cartridge is inserted into a carriage that transports the cartridge into a detection chamber. Analytical regions on the cartridge are read by sequentially passing them between a light source and a light detector. Often the analytical regions are passed through the detection system by motorized transport of the cartridge on a carriage system. Alternately, the cartridge remains stationary while the detection system is transported along the cartridge.

Other old art systems employ video scanners (e.g., CCD sensors) to read an array of analytical regions on a cartridge. However, optics and required offset distances make the devices more expensive and bulky.

There are many problems with such systems. The old art systems are not portable, so they typically remain at a central laboratory and samples must be transported for analysis. The old systems are complicated, e.g., with the motors and many moving parts, so are prone to breakdown. The old systems are expensive because of their overall size and numerous bulky components.

In view of the above, a need exists for a handheld assay reader of simple design. It would be desirable to have an assay reader able to read an array of results with fewer moving parts. Benefits could also be realized through use of reliable micro-scale components in a small sized device that is rugged and inexpensive. The present invention provides these and other features that will be apparent upon review of the following.

SUMMARY OF THE INVENTION

The present devices and methods employ one or more pivoting mirrors to scan an array of analytical regions for detection of an analyte of interest. In general methods of reading arrays in a hand held analytical device, an array of analytical regions comprising reaction products of an analyte and reagent are generally illuminated. Light from individual analytical regions is reflected from the region to a light detector that provides output correlated to the quantity of reaction product present in the analytical region. In another aspect, light is scanned onto a 2 dimensional array of analytical regions from a light source by reflecting the light off of two mirrors having non-parallel pivot axes. Alternately, one or more pivotable mirrors direct light from a light source sequentially on to individual analytical regions with detection using a broadly directed detector. In certain embodiments, light from the light source to the array, and from the array to the detector, is reflected off one or more pivotable mirrors. In a preferred embodiment, one or more mirrors and detector are mounted in a hand held analytical cartridge reader, and the cartridge includes three or more analytical regions in a planar array.

An exemplary analytical device of the invention can include, e.g., a pivotable mirror comprising two pivot axes, a first actuator configured to pivot the mirror on a first of the two axes, a second actuator configured to pivot the mirror on a second of the two axes, an array of three or more analytical regions which are not aligned along a straight line (e.g., a 2D array), and a light detector oriented to receive light from the mirror. By tilting the mirror about the two axes, light from each of the three regions can be sequentially reflected to the detector. In preferred embodiments, the mirror is a micromirror and the first pivot axis is substantially perpendicular to the second pivot axis. In an embodiment, light received at the detector has not reflected off of any single mirror more than once and a mirror sequentially reflects light from each of the three regions to the detector without relative motion between the detector and the regions. Light received by the detector reflected from the mirror can be any light from the array, e.g., associated with an analyte of interest, such as light previously reflected from one of the analytical regions, light transmitted through one of the analytical regions and fluorescent emissions from one of the analytical regions. Light energy to illuminate the array analytical regions can be from any appropriate light source, such as, e.g., an LED, laser, incandescent lamp, a fluorescent lamp, and the like.

In another embodiment of the device, light is scanned onto the detector from the array using paired pivotable mirrors. For example, the analytical device can include two pivotably mounted micromirrors and a light detector. The components can be arranged so that there is a light path from a first of the two micro mirrors to a second of the two micromirrors on to the light detector. In one aspect, the pivot axis of the first of the two micromirrors is substantially perpendicular to the pivot axis of the second of the two micromirrors. In some embodiments, the two micromirrors are fabricated on the same substrate and remain together on the same substrate. In certain embodiments, actuators are configured to pivot the first of the two micromirrors on one or more pivot axis, and actuators configured to pivot the second of the two micromirrors on one or more pivot axis. It is preferred that the first and/or second micromirror comprises a first pivot axis mount and a second pivot axis mount, whereby the first and/or second micromirror can be pivoted with 2 degrees of freedom. In another preferred embodiment, the first micromirror and the second micromirror each have pivot mounts at two axes, whereby both micromirrors can be pivoted with two degrees of freedom.

The analytical device can include a micromirror pivotably mounted to a substrate through a first pivot axis and through a second pivot axis, with the light detector oriented to receive light reflected directly from the micromirror. The pivot axes can be mounted with a torsion bar to provide selectable infinitely variable pivot angles, e.g., depending on the amount of turning force applied by the associated actuator. The device components can be arranged with a geometry allowing the mirror to pivot through an angle that reflects light from an analytical region of an analytical cartridge onto the detector.

Actuators can be positioned to interact with the mirror(s) providing force to pivot them about their pivot axis. For example, the actuators can be electromagnetic devices, electrostatic devices, thermal actuators, annular vertical comb actuators, and/or the like. The Actuators can be configured to provide digital (e.g., two position flipping) positioning, or analog positioning (e.g., infinitely variable positioning throughout a pivot range). For example, the pivot mount defining a pivot axis of the mirror can have a torsion bar so that the pivot angle of the mirror depends on the amount of force or energy applied by the actuator to turn the mirror. Alternately, any pivot angle can be selected in increments, e.g., by use of a stepper motor, or the like. For the scanning embodiments, it is preferred that the actuators are configured to provide infinitely variable pivoting about the at least one of the axes.

The device can detect light from an array of two or more analytical regions. The arrays can be linear arrays of two or more analytical regions, or planar 2D arrays of three or more analytical regions. The devices can optionally pivot to scan three dimensional arrays of analytical regions. The analytical regions can include an array of two or more different reagents or ligands, e.g., in embodiments wherein a single sample is tested for more than one different analyte. In many embodiments, three or more analytical regions are not arranged in a straight line, and a light path is provided running from one of the regions to the light detector, reflecting off of a first mirror and off of second mirror.

Methods of detecting assay results are an aspect of the inventions. For example, a method of detecting assay results on a two dimensional array can include illuminating one or more analytical regions on the array, and reflecting light from the one or more analytical regions from a first mirror onto a light detector. Optionally, the method of detecting assay results on a two dimensional array can include reflecting light from a light source to the one or more analytical regions from a first mirror to illuminate the region. The first mirror can have a first pivotable mount defining a first pivotable axis and a second pivotable mount defining a second pivotable mount substantially perpendicular to the first axis. Light from the one or more analytical regions can travel from the one or more regions, or from the light source, directly to the mirror. The method can include reflecting the light off a second mirror between the light source and the regions and/or the one or more regions and the detector.

Methods can include selectively scanning light onto an array. For example, a method of scanning light onto a 2D analytical array can include directing a beam of light onto a first pivotable mirror comprising a first pivotable axis, reflecting the beam of light from the first mirror to a second pivotable mirror having a second pivotable axis not parallel to the first pivotable axis, reflecting the beam of light from the second mirror on to a first analytical region of an array of analytical regions, and pivoting the first mirror on the first axis to redirect the beam to a second analytical region of the array or pivoting the second mirror on the second axis to redirect the beam to the second analytical region of the array. Optionally, both the first mirror and the second mirror can be pivoted to redirect the beam to the second analytical region of the array. Optionally, the first mirror and/or the second mirror can each be pivoted on two or more axes to redirect the beam to the second analytical region of the array. The pivotable axes can be defined by mounting the first mirror or the second mirror on one or more pivotable mounts.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "an actuator" can include one or more actuators, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

A "pivot axis" is as known in the art. For example, a pivot axis is a line running through a point of rotation of an object perpendicular to the plane of an arc defined by the movement of a point in the object outside the point of rotation. Mirrors of the invention are often pivotably mounted so that they can rotate about an axis defined by the pivotable mount. In some cases a mirror can have two pivotable mounts defining two pivot axes, thereby allowing the mirror to sequentially and/or simultaneously pivot on the two axes (e.g., X-Y scanning). Scanning by turning a mirror through one pivot axis can read a planar surface in a scanning path describing a line (one dimension). Scanning by turning a mirror through two pivot axes can read (e.g., receive light from and reflect on to a detector) a planar surface in a two dimensional scanning path.

A mirror mounted to pivot on only one pivot axis has one degree of freedom of motion. A mirror mounted to pivot on two different pivot axes can move with two degrees of freedom.

An "actuator" applies force to move an object. Typically, actuators of the invention apply a force to a mirror or mirror mount, resulting in the mirror pivoting through an angle about a pivot axis.

An "analytical region", as used herein, refers to a region from which an analytical signal, e.g., associated with a putative analyte of interest, is generated and can be detected. Typically, e.g., an analytical region emits a quantity of light directly or indirectly correlated to an amount of analyte present in an analyzed sample. For example, a colored or fluorescent analyte can be directly detected at an analytical region having a capture antibody specific for the analyte. Optionally, a reaction product of the analyte can be presented at an analytical region for indirect detection of the analyte.

Pivoting of a mirror is "infinitely variable" when it is mounted on a pivot axis with an actuator configured to controllably provide a continuous series of positions through the pivot range of the mirror's pivot mount. Mirrors mounted to provide three or more selectable pivot angles can be considered to have incrementally variable pivoting. A digital mirror, configured to flip between two positions about an axis, is not considered to have infinitely variable positioning on the axis because it is configured to controllably provide alternately only one or the other of two mirror positions on the axis.

An "analyte" of interest is a molecule putatively present in a sample, as is understood in the art. For example, many analytes are molecules of clinical interest possibly present in clinical specimens, such as blood. Analytes are detected directly or indirectly through detection of light coming from an analytical region in devices of the invention.

Light travels "directly" between two device components when it travels in a straight line between the components. For example, light does not travel directly to a detector from a mirror if it reflects off a surface in the light path between the mirror and detector. A "light path" is the path traveled by light between two points, including changes of direction caused by, e.g., reflection and refraction.

Scanning, as used herein, refers to pivoting a mirror on one or more pivot axis to reflect light between a point (e.g., light source or detector) and a series of points (e.g., analytical regions) along a series of different light paths. Two dimensional scanning refers to scanning with one or more mirrors so that light reflected to a certain point (e.g., a detector surface) originates from locations in light paths that are in different planes.

A "light path" is the route taken by light (e.g., a beam of light). Light travels in a straight line. For example, the light path directly between two points can be a straight line. However, in many situations, a light path between two locations can include reflections and refractions that change the direction of light propagation, thereby providing a light path that is not a straight line.

A "micromirror" is a micro-scale mirror. For example, micromirrors have a reflecting surface with at least one dimension less than 1 mm. Micromirrors can have at least one dimension less than 1 mm and more than about 1 µm, from about 500 µm to about 5 µm, from about 100 µm to about 10 µm, or from about 50 µm to about 25 µm.

As used herein, the term "microfluidic" refers to systems or devices having a fluid flow channel with at least one cross sectional dimension less than 1000 µm. Most microfluidic channels allow capillary flow, e.g., depending on the affinity of a particular fluid for the channel walls. Some functionally capillary scale channels can be greater than microfluidic scale. For example, a microfluidic channel can have a cross-sectional dimension of 500 µm or less, 300 µm or less, 100 µm or less, 50 µm or less, or 10 µm or less. In many embodiments, the channel dimension is about 50 µm to 100 µm, but typically not less than 1 µm.

Capillarity is a general term known in the art referring to phenomena attributable to the forces of surface or interfacial tension. A capillary scale chamber or channel has at least one dimension that functionally results in flow of an intended fluid along the chamber of channel surface by capillary action. Capillary scale chambers and channels of the invention can be at a microfluidic scale or not.

As used herein, "substantially" refers to largely or predominantly, but not necessarily entirely, that which is specified. The term "about", as used herein, indicates the value of a given quantity can include quantities ranging within 10% of the stated value, or optionally within 5% of the value, or in some embodiments within 1% of the value.

BRIEF DESCRIPTION OF THE DRAWINGS

FIG. 9 is a chart showing MEMS technologies with regard to typical optical mirror size employed.

FIG. 10 shows a schematic representation of bulk micromachining processing by DUE.

DETAILED DESCRIPTION

Methods and devices use pivoting mirrors to scan analytical regions directing light between the regions and a light detector and/or between the regions and a light source. For example, a microfluidic analytical cartridge can flow sample analyte to react with a reagent followed by capture of the reaction product at an analytical region for detection. The analytical region can be illuminated with light that interacts with the reaction product to provide a signature light output, such as a fluorescence or absorbance pattern. Optionally, the illumination is provided as a sequential scan reflecting off pivotable mirrors from a light source. The light output from the analytical region can be reflected off a mirror oriented to provide a light path between the analytical region and the light detector, which transfers a proportionate electronic signal to a microprocessor for analysis or storage. Actuators then pivot the mirror about one or more pivot axes to provide a new light path to the detector from another analytical region. Two-dimensional (2D) arrays of analytical regions can be sequentially scanned using one or more mirrors mounted on two or more non-parallel pivot axes.

Methods of Reading Assay Arrays

An array of analytical regions on an analytical cartridge can be read by illuminating the array members and directing resultant emissions from the analytical regions to a detector using one or more pivotable mirrors.

Illuminating the array can be by any light source appropriate to the detection scheme. Typically, in portable devices, the light source is a light emitting diode (LED). Illuminating can be by generally illuminating the entire array, or analytical regions can be illuminated one at a time, e.g., as they are to be read.

Illumination or detection scanning techniques can depend on the layout of the analytical region array. An array of analytical regions can be a linear array of regions, e.g., arranged along a straight microchannel. In many embodiments, the array of analytical regions is arranged in a 2D plane, e.g., to hold more regions in a smaller space. Light emissions from a linear array of regions can often be directed to a detector using a mirror with a single pivot axis or using multiple mirrors with parallel pivot axes. In embodiments with regions arrayed in two dimensions, each region can be scanned into the detector, e.g., using a single mirror with at least two degrees of freedom of movement and/or using two or more mirrors mounted to pivot on different non-parallel pivot axes. In order to scan through angles greater than the pivotable range of a single mirror, the light path can include reflection off of two or more mirrors, compounding the reflection angles over a broader range than provided by one mirror alone.

Figure 1:
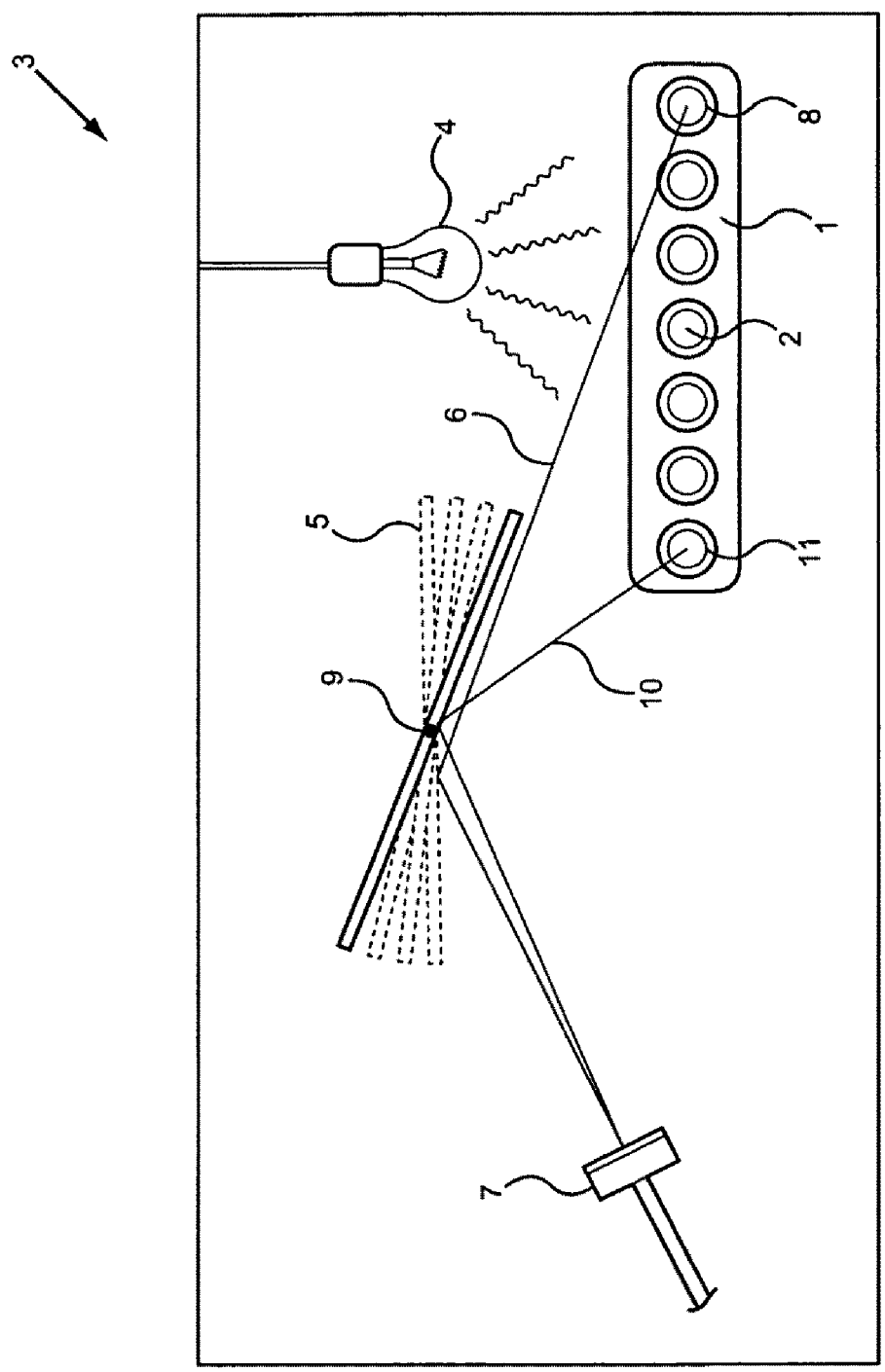
FIG. 1 is a schematic diagram showing an analytical device providing scans of a linear analytical region array.

Scanning a linear array of analytical regions can be, e.g., as shown in FIG. 1. A cartridge 1, including a number of analytical regions 2, can be inserted into analytical device 3 and illuminated by light source 4. Light from individual regions can reflect off of mirror 5 in a first position at an angle providing a first light path 6 to a light detector 7 only from a first region 8. The mirror can be pivoted on pivot axis 9 to a second position at an angle providing a light path 10 to the light detector only from a second region 11. In embodiments wherein light is scanned on to the regions and generally read by a detector, the system can be configured with light source 4 replaced with a light detector and light detector 7 replaced with a light source. In certain embodiments, element 4 is excluded while both light provision and detection take place at element 7.

Figure 2:
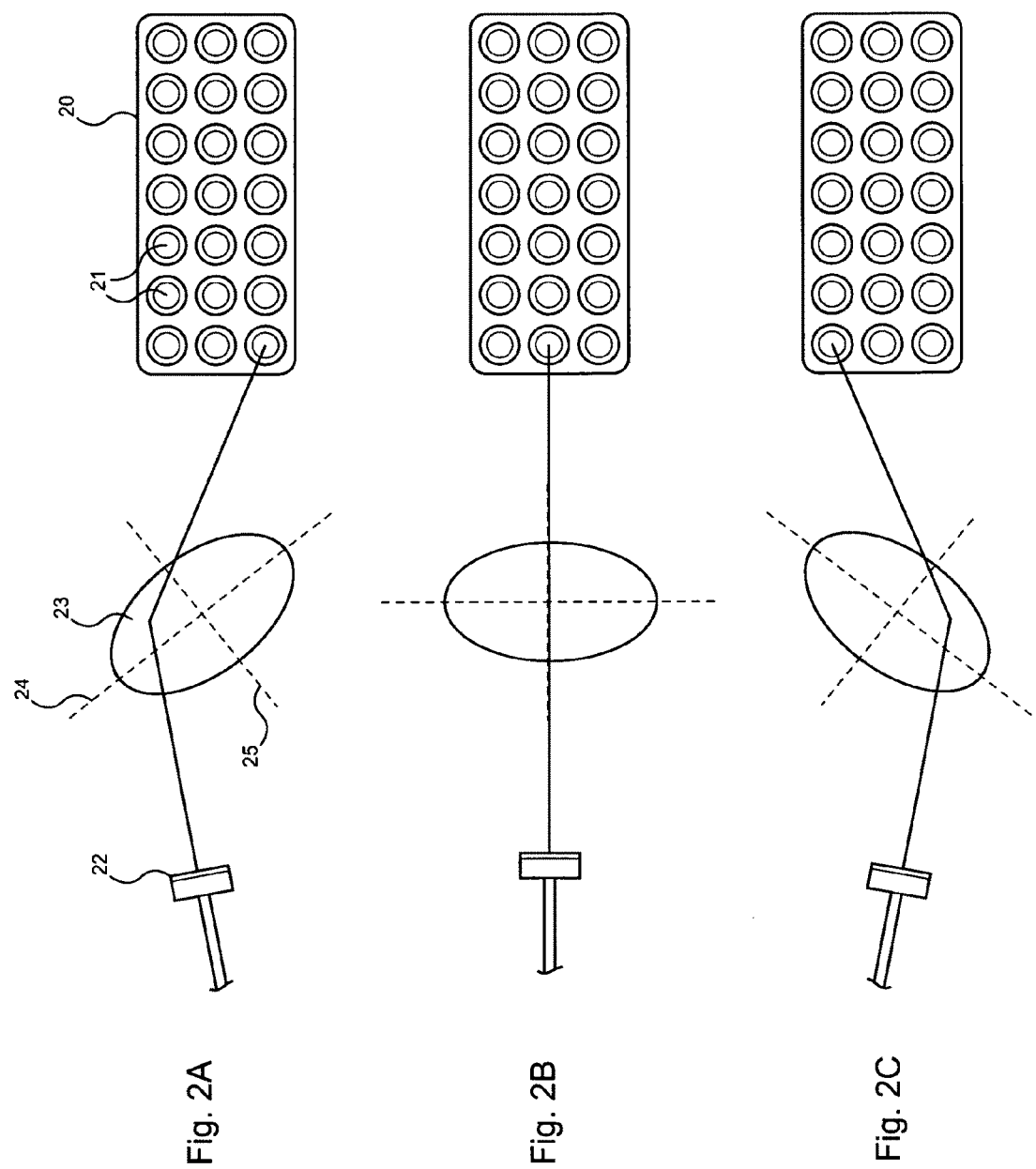
FIGS. 2A to 2C are schematic diagrams showing methods of scanning a 2D analytical region array using a mirror mounted to pivot on two axes.

Scanning a 2D array of analytical regions can be as shown, e.g., in FIG. 2. An analytical cartridge 20 can include a 2D array of analytical regions 21. Light emanating from the a particular region can be individually directed to a light detector 22 by mirror 23 depending on the tilt of the mirror about a first pivot axis 24 and/or second pivot axis 25. For example, as shown in FIG. 2A, the mirror can be tilted down to the right on the first pivot axis to direct light from the left of the array to the light detector. The mirror can be pivoted both: 1) down at the top on the second pivot axis; and 2) down to the right on the first pivot axis, to direct light from a bottom left array region to the light detector, as shown in FIG. 2C. By pivoting the mirror less down right on the first pivot axis and pivoting bottom down on the second pivot axis, the light detector can receive light emanating from a center top array region, as shown in FIG. 2B. Of course, the relative tilt along each of two axes required to direct light to the detector will depend on the geometry of the pivot axes and relative positions of the detector, mirror and regions, as is known in the art. Light can be scanned on to the regions by replacing detector 22 with a light source or by adding a light source at position 22.

The analytical regions can be illuminated with any appropriate light source, e.g., depending on the intensity, frequency and dispersal desired for a particular device and analytical mode of operation. In many embodiments, it is desirable to generally illuminate an entire array at once from a single light source, e.g., to provide consistent illumination at each region without the requirement of mechanical systems to redirect the light or move the array for each detection. For example, a single incandescent lamp, array of LEDs or an LED with a dispersing lens can illuminate an entire array at once. Alternately, coherent light can be directed to individual analytical regions of an array, in turn, e.g., using scanning mirrors, as described herein. To provide a uniquely detectable signature against ambient background light, the illumination can have, e.g., a unique frequency, frequency combination or frequency modulation.

By reflecting light from individual array regions to a detector, the detector and array can stay stationary, relative to each other, while allowing separate detection of each region by merely changing the tilt of a mirror in the light path between the array and detector. Those of skill in optics and geometry have long known that the angle of incidence equals the angle of reflection for light reflecting off a reflective surface. Because a change of incident angle results in a concomitant change in reflective angle, moving the reflective surface through an angle results in twice the change in the light path angle. Therefore, pivoting a mirror provides a 2-fold benefit in changing a light path angle. In many embodiments, a mirror is mounted on two or more pivot axes, allowing the mirror to scan through three dimensional space to receive light from any point (or direct light on to any point), e.g., on a two dimensional planar surface (e.g., a planar array). In preferred embodiments, the mirror is mounted on pivotable mounts aligned perpendicular to each other, thereby allowing a full range of scanning potential, e.g., along a line, plane or volume (e.g., layered array) of separate analytical regions.

The methods include reflecting light in a path between two or more mirrors. In some embodiments, light from the analytical regions travels on a light path reflecting off two or more mirrors on the way to the detector. In some embodiments, light from a light source travels on a light path reflecting off two or more mirrors on the way to the analytical regions. Provision of more than one mirror can be useful, e.g., in redirecting light to optional detector locations, further compounding reflection angles, lengthening light paths, allowing 2D scanning from mirrors each having only one pivot axis mount, and/or the like. For example, where design constraints require the detector to be located behind a first mirror, a second mirror can be used to redirect light from the first mirror to the detector. Where a mirror is only capable of tilting, e.g., through an angle of 10 degrees, a pair of the mirrors can interact to provide an overall pivot of 20 degrees (and an effective light deflection range of, e.g., 40 degrees). Paired mirrors can lengthen a light path, e.g., to provide a wider scanning sweep in a smaller package using the same range of mirror tilt. Scanning light from an array of analytical regions can be accomplished using two single-pivoting mirrors. For example, a first mirror can scan an "X" direction to reflect light onto a second mirror that can scan in the "Y" direction, thereby defining light paths that can sequentially feed light from all regions of a 2D array to a detector.

Methods of detecting light can be any appropriate to the light intended for detection. For example, a detector can be configured to have the appropriate sensitivity and frequency range. The detector can be located at an angle and distance from the mirrors to provide the desired scanning range and precision. Detectors can be fitted with an aperture, e.g., slit or annulus that limits the beam width with received from the mirror(s) or can have a concentrator that focuses a broad beam onto a smaller detector surface. Typically, detectors can be mounted at a constant position relative to the analytical regions and/or mirror(s). Optionally, the detector can be mounted, e.g., on a carriage or pivot that allows the detector to move relative to the mirrors and/or analytical regions.

Detectors typically provide an output proportional to light input. In many embodiments, the output is an analog voltage signal (e.g., photodiode or photomultiplier tube output). Such a signal can be transferred to an analog to digital converter and the digital information stored in a digital device, such as a computer for direct read out, data analysis, or storage.

In one example of a method of scanning assay results, a sample containing several peptide analytes of interest is placed into the sample port of a microfluidic analytical cartridge. The sample is filtered and flows by capillary action through a channel to a reaction chamber where the analyte comes into contact with a reagent that reacts with the peptides to convert them into fluorescent reaction products. The reaction products continue flowing by capillary action to a detection chamber comprising an array of analytical regions. Each analytical region can include a different affinity molecule that specifically captures a different peptide of interest, e.g., at a different position in an array of analytical regions. The analytical cartridge is placed into a receptacle in a hand held analytical device and illuminated by a light source providing an excitation wavelength. The cartridge remains stationary while a micromirror pivots to sequentially reflect light from each of the analytical regions onto a detector sensitive to the emission wavelengths of the captured fluorescent peptide products. The detector provides a voltage output proportional to the amount of reaction product present at each analytical region. The voltage output is transferred to an analog to digital converter, and the output of the converter is received by a digital device where the data is stored and analyzed. The digital device displays an assay result depending on the amount of each peptide of interest present in the original sample.

Analytical Devices with a 2D Scanning Mirror

Devices of the invention include scanning mirrors that receive light from analytical regions and reflect the light on to a detector, and/or that receive light from a light source and reflect the light on to an analytical region. The light from the analytical regions is correlated to an analytical result, e.g., obtained from illuminating the reaction product of an analyte and reagent at the analytical region. In a preferred embodiment, a hand held device has a station to receive an analytical cartridge having analytical regions, a light to illuminate one or more of the analytical regions, one or more pivotable mirrors to receive light from one or more of the analytical regions, and one or more detectors onto which the mirrors can be oriented to reflect the light from the one or more analytical regions. A signal can be generated by the detector in response to the received light, and the signal can be transferred to an analysis, display, and/or storage device. Optionally, one or more pivotable mirrors can be used to scan light on to the analytical regions from the light source.

Cartridges and Analytical Region Arrays

In many devices of the invention, pivotable mirrors reflect light from an analytical region of an analytical cartridge onto a detector to provide an analytical result. The analytical cartridge can be an integral part of the analytical device, or can be removable and exchangeable. The cartridge can be a simple "dipstick" or can be a complex device in itself, with fluid handling features, such as, e.g., the ports, chambers, channels, reagents, accessories and valves (e.g., a microfluidic cartridge).

Locations on an analytical cartridge or dipstick wherein light emanates according to an analytical scheme to indicate the presence and/or quantity of an analyte of interest in a sample tested by the cartridge or dipstick are considered to be analytical regions. In a simple form, the analyte of interest itself can have a characteristic light absorbance, transmittance, or fluorescence (e.g., porphyrins, bilirubin or carboxyhemoglobin) that can be detected at an analytical region. However, in most instances the light correlated to the analyte of interest emanates from a reaction product of the analyte, e.g., with a reagent. For example, in some embodiments, a sample containing the analyte of interest can contact a reagent at the analytical region to react, forming a detectable reaction product at the analytical region. In other embodiments, the analyte of interest can react with a reagent at a location remote from the analytical region and the reaction product can be transferred to the analytical region for detection. Reagents can include, e.g., chromogens, affinity molecules, antibodies, monoclonal antibodies, enzymes, enzyme substrates, and/or the like, associated with a particular analytical method.

Figure 3:
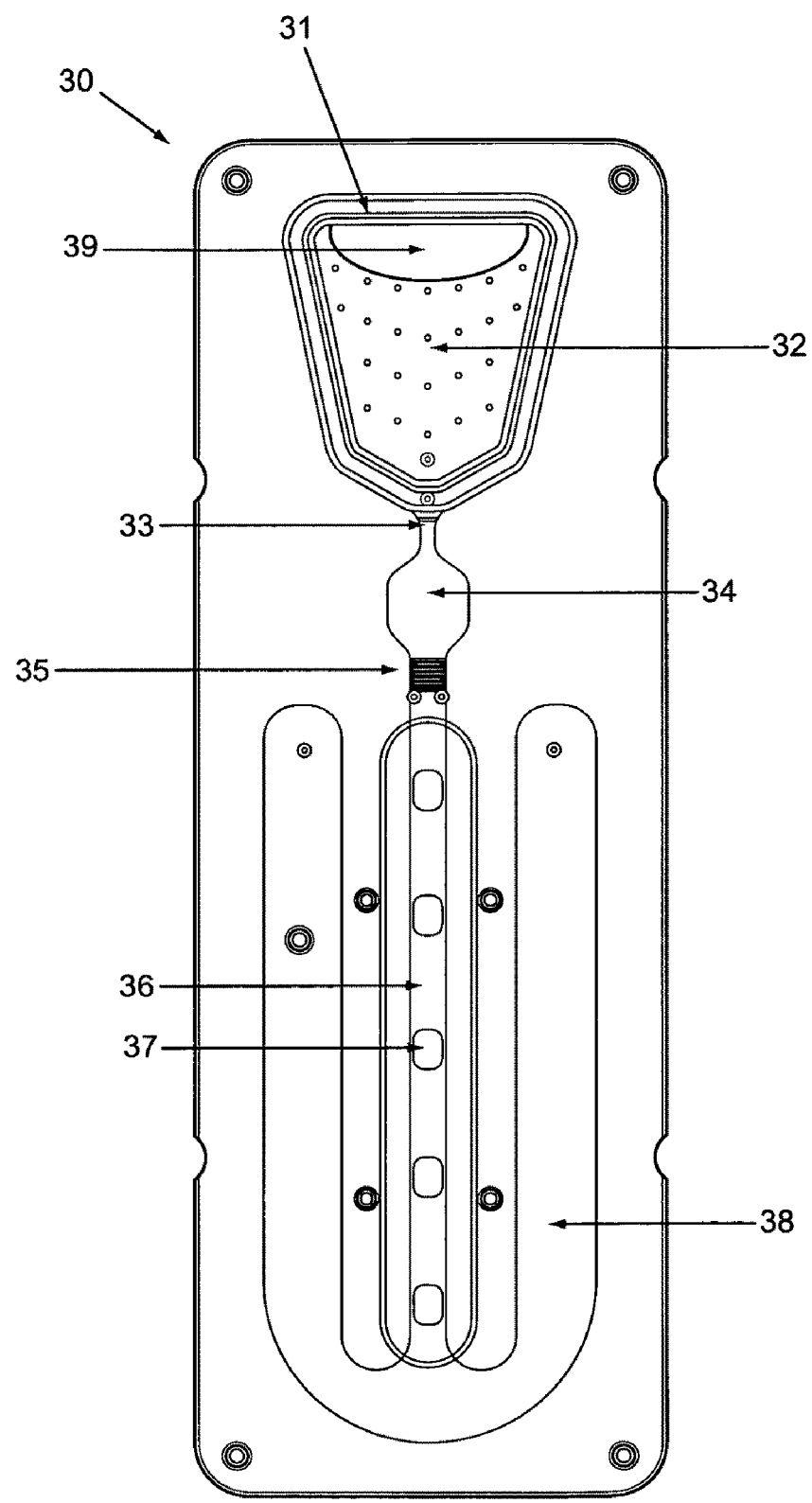
FIG. 3 shows a schematic diagram of an analytical cartridge having a linear array of analytical regions.

An exemplary analytical cartridge, having a linear array of analytical regions is presented in FIG. 3. Cartridge 30 includes compartments and channels in sequential fluid contact. Filter chamber 31 includes filter element 32 in fluid contact with incubation chamber 34 through back diffusion barrier 33. Exit of a fluid from the incubation chamber is regulated by flow modulator 35, which eventually releases reaction products from the incubation chamber into detection channel 36. The detection channel can includes a linear array of analytical regions 37 on a substrate where further reactions and/or detection can take place. Finally, the cartridge can include one or more vented waste chambers 38 configured to receive expended sample, reagent, and/or rinse solutions, as required. Fluids can move through this cartridge by capillary action.

Figure 4:
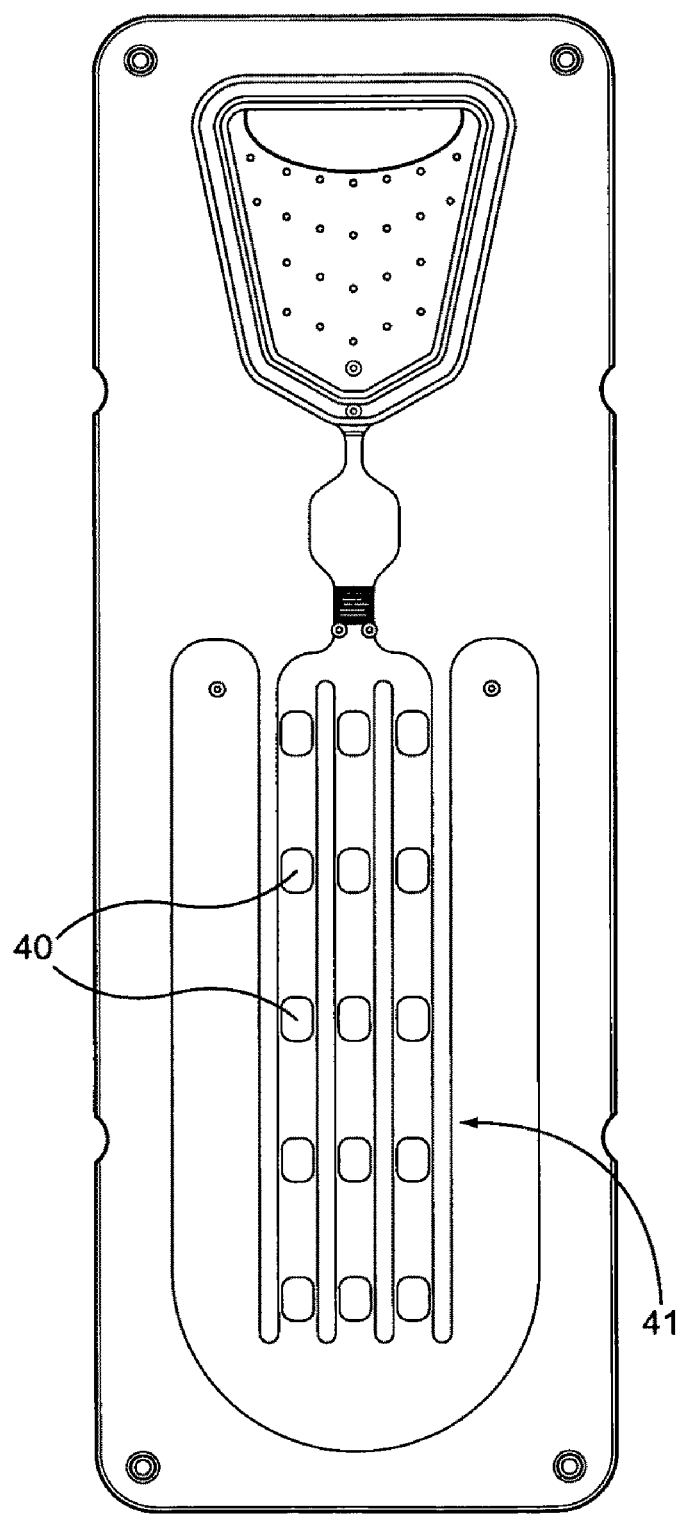
FIG. 4 shows a schematic diagram of an analytical cartridge having a 2D array of analytical regions.

In another example, as shown in FIG. 4, the analytical regions 40 can be provided in a in a 2D array 41. The array can receive analyte or reaction product in parallel flow channels, as shown, in a sequential (e.g., serpentine) path, or in a single broad fronted path across the broad array in a single detection channel.

Pivotable Mirrors

Pivotable mirrors of the devices are typically mounted in a frame (e.g., integral to a unitized analytical device) at one or two pivotable mounts. Usually, the mounts comprise a pair of pivot mount hardware units, such as gimbals, at opposite sides of the mirror, e.g., defining a pivot axis essentially in the plane and running through the center of the mirror or reflective surface. Optionally the pivot axis can run other than through the center or plane of the mirror, e.g., offset from the center within the mirror, or can be remote from the mirror (e.g., pivoting on a frame extension from the mirror). Actuators can be provided to pivot the mirrors about the axes.

The mirrors can be macro-scale mirrors and/or micromirrors. For example, macro-scale mirrors can range in size from having a reflective surface with at least one dimension of about 10 cm or greater to more than about 1 mm, from about 5 cm to 2 mm, from about 2 cm to 5 mm, or about 1 cm. Micromirrors can have a reflecting surface with at least one dimension less than 1 mm. Micromirrors can have at least one reflecting surface dimension less than 1 mm and more than about 1 µm, from about 500 µm to about 5 µm, from about 100 µm to about 10 µm, or from about 50 µm to about 25 µm. In many cases, length and width of the reflecting surface are of similar or the same scale.

The pivotable mirrors typically have a planar reflecting surface. However, the reflecting surface can optionally be, e.g., convex, concave, parabolic, hemispherical, and/or the like. The surface is typically smooth, entire and uniform. Alternately, the mirrors can have perforations or surface textures.

Pivot axes of pivotable mirrors are functionally defined by the one or more pivot axis mount structures. Optionally, one or more mirrors in the analytical devices of the invention can be mounted with a stationary mount, e.g., so the mirror can not pivot (and, therefore is not pivotably mounted and does not have a pivot axis). Optionally, a mirror is mounted using a single pivot mount to define a pivot axis, however, pivot axes are typically defined by paired pivot mounts, thereby typically providing enhanced mounting strength and pivoting precision.

Figure 5:
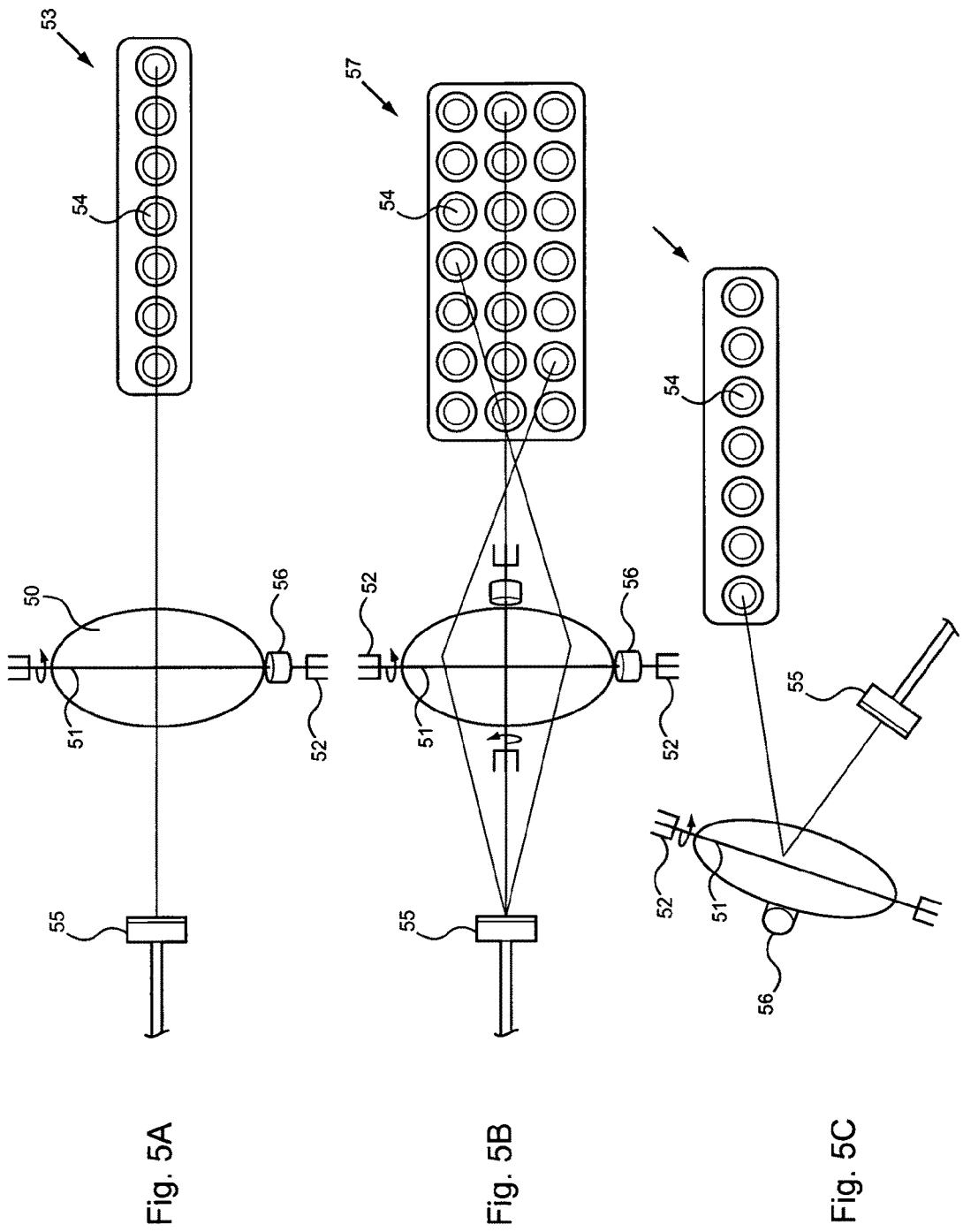
FIGS. 5A to 5C are schematic diagrams showing exemplary configurations of mirrors providing scanning light paths between assay arrays and detectors (or optionally, light sources).

Devices can include a single mirror having a single pivot axis, as shown, e.g., in FIGS. 5A and 5C. Mirror 50 has pivot axis 51 defined by a pair of pivot mounts 52 so that light from linear array 53 analytical regions 54 can be sequentially reflected onto detector 55 in response to turning forces provided by actuator 56.

Optionally, devices can include a single mirror having two pivot axes 51, allowing two degrees of freedom in pivoting motion so that light from a 2D array 57 of analytical regions 54 can be sequentially scanned onto the detector 55, as shown in FIG. 5B.

Figure 6:
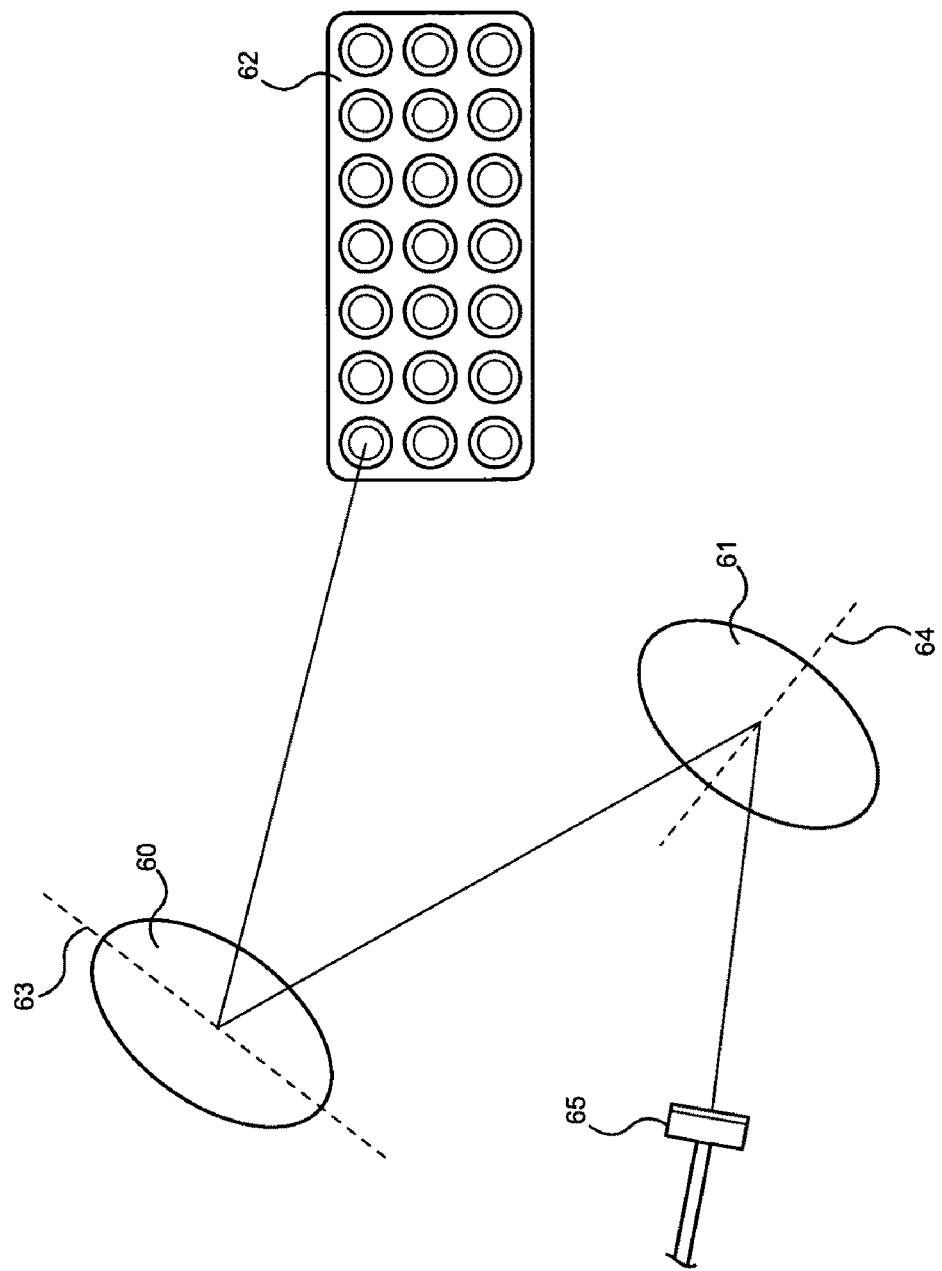
FIG. 6 is a schematic diagram of a two mirror system for 2D scanning of a planar analytical region array.

In still other analytical devices, two or more mirrors can be used to direct light from the analytical regions to the detector. For example, as shown in FIG. 6, a first mirror 60 can reflect light to second mirror 61 from analytical region array 62. The pivot axis 63 of the first mirror is substantially perpendicular to the pivot axis 64 of the second mirror so that the combined mirrors can scan planar surfaces (such as the planar array 62), e.g., up-down and left-right to reflect light sequentially from (or to) any member of the array to detector 65.

Figure 7:
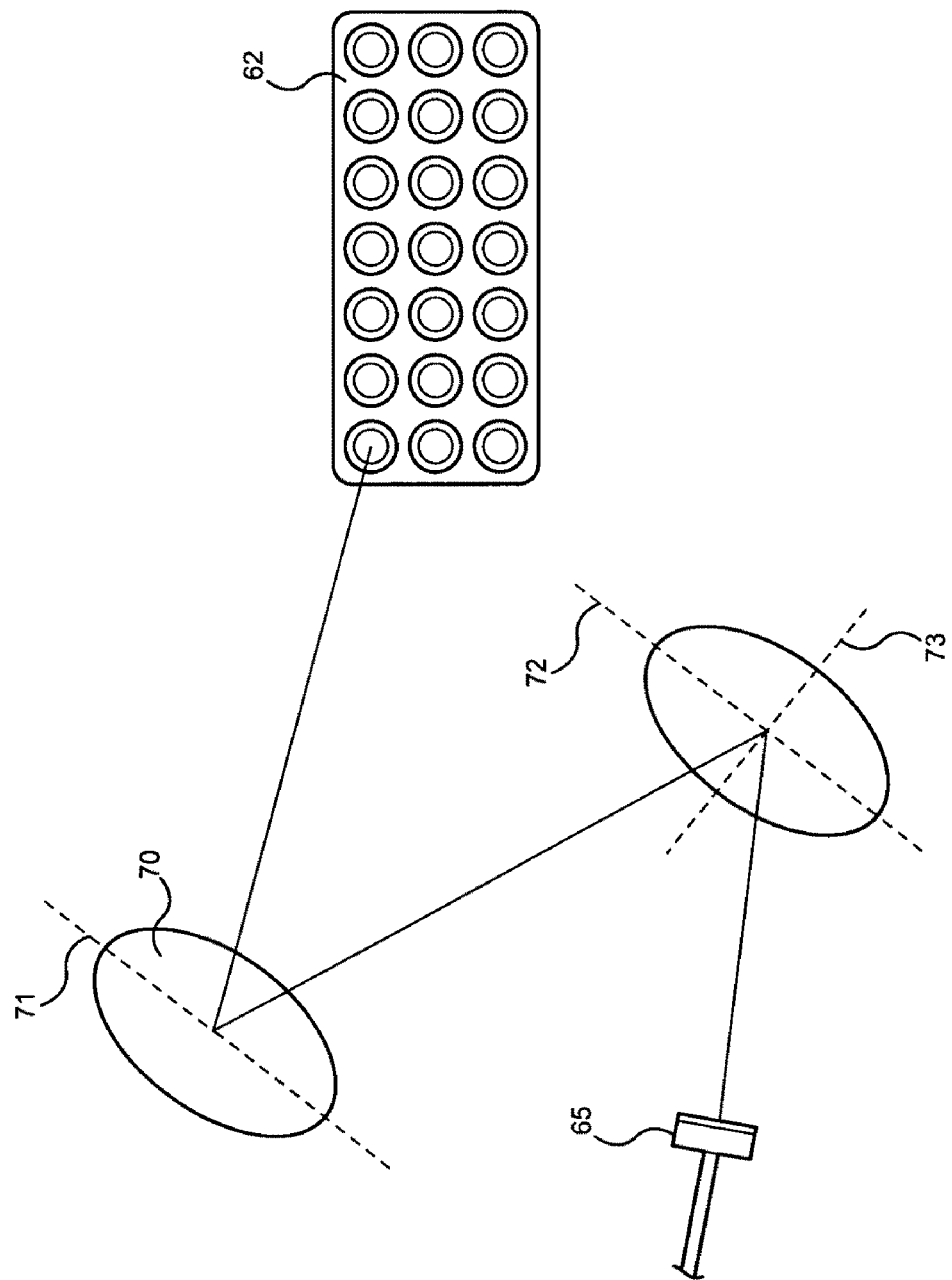
FIG. 7 is a schematic diagram of a two mirror system for 2D scanning of a planar analytical region array, wherein at least one minor has at least 2 degrees of freedom to pivot.

In other devices, two mirrors and interact to provide 2D scanning and compounded scanning angle ranges. Where the two mirrors have non-parallel pivot axes of rotation, the combined mirrors will possess a 2D scanning ability, the range of which depends on the trigonometry of the axes (e.g., the greater the sine of the acute angle between the axes, the greater the 2D scanning area). The more parallel the pivot axes between the two mirrors, the more they can compound their combined scanning angle (e.g., the less the sine of the acute angle between the axes, the greater the scanning range in a dimension across their pivot axes). For example, as shown in FIG. 7, a first mirror 70 can be mounted with a first pivot axis 71 and the second mirror mounted with a pair of perpendicular pivot axes 72 and 73; axis 72 of the second mirror being parallel to axis 71 of the first mirror. In such a case, pivoting of the second mirror can provide 2D scanning. In addition, the combination of pivoting around axis 71 and axis 72 can beneficially compound the scan angle (sweep) of the established light path in a dimension perpendicular to the axes (alternately, where the two mirrors pivot in the same direction, the angle change of the second mirror can tend to neutralize the angle change of the first mirror). In other embodiments, the first mirror can have two pivot axes and the second mirror can have one pivot axis, or both mirrors can have two pivot axes.

Actuators are typically associated with the mirrors in order to make them move through their pivotable range. The actuators typically receive electrical energy, although they can receive mechanical, hydraulic, light, heat, pneumatic energy, and/or the like. Preferred actuators include, e.g., an electromagnetic device, an electrostatic device, a thermal actuator, an annular vertical comb actuator, and/or the like. The actuators convert energy to work moving the associated mirror. The actuator can be mounted, e.g., at the pivot mount and provide angular force (torque), or mounted to a point offset from the pivot axis to provide a linear force that tilts the mirror on the axis.

The character of mirror pivot action can be digital or analog. A mirror that is mounted and actuated, e.g., to alternate only between two pivot positions (1 and 0) in use can be a digitally configured pivotable mirror. For example, an actuator can be configured to force a mirror to flip from one side if its range to the other side in a digital mode (e.g., without structures that function to controllably provide intermediate hold or functional progressive scan positions). Optionally, a mirror can have analog motion, e.g., with an ability to pivot and controllably maintain any (e.g., infinitely variable) pivot angle through its range of motion. Optionally, an actuator can work against a spring component, wherein greater force provides a greater pivot angle. A gradient of force can provide a gradient of selectable pivot positions for the mirror, e.g., between the ends of motion range. In one embodiment, the pivot mount of a mirror has a torsion bar that increases counter force as it is twisted through greater angles. An actuator is provided with controllable variable force so that an amount of force can be selected to provide any desired amount of pivot against the torsion bar. Alternately, the actuator can have a controllable "throw", e.g., so that a freely pivoting mirror can be positioned depending on the length of the actuator extension. For example, the actuator can have a threaded screw discretely controllable with a stepper motor, or have a monitor system can feed back to a position controller to provide a desired infinitely variable mirror position. Of course, a digital mirror is configured to flip quickly between two position options, but is not configured for selection of other positions between the two positions. Whereas, an analog mirror is configured to selectively maintain or controllably progress through its range of motion, e.g., having more than two controllable position options.

Light Sources for Illumination of Analytical Regions

For detection of analytes and/or reaction products in an analytical region, the region is typically illuminated from a light source. Optionally, light can emanate from an analytical region due to chemoluminescence, phosphorescence, nuclear radiation, and/or the like. Light can be provided directly from a light source, or can be propagated through a light path including, e.g., optic cables, lenses, mirrors, and/or the like. The light source can be, e.g., a laser, LED, tungsten lamp, Hg vapor lamp, sodium vapor lamp, fluorescent lamp, noble gas lamp, and/or the like.

In many embodiments, a light source is positioned to generally illuminate the whole array of analytical regions at once. For example, an incandescent light, or LED with diffusing optics can be positioned above or behind a planar array of regions to illuminate each array member at once.

It is an aspect of the invention that light can be selectively scanned from a light source onto the array of analytical regions, e.g., using mirror arrangements described herein for scanning light from analytical region arrays onto a detector. For example, a "light source" can be added to or substituted for the "detector" described herein, and shown in the Figures herein, to provide linear and/or 2D scans of light onto the arrays from the light source.

It is envisioned that a light source and detector can be mounted near each other, or in the same position, so that light can be scanned onto the analytical region array members using the same system of pivotable mirrors to return light from the array members to the detector (e.g., along substantially the same or similar light paths).

Hand Held Devices

The analytical systems are well suited to hand held embodiments, e.g., wherein analyses can be carried out at remote locations and data can be downloaded to a computer system at the convenience of the user.

Because the pivoting mirrors can be quite small while providing large scanning ranges with precision, they can enable relatively small analytical devices. Moreover, specific illumination scanning and/or detection scanning with the mirrors can be very energy efficient.

Hand held devices can include a housing conforming to hand gripping and providing protection against the environment. The device can have a slot to receive microfluidic cartridges or analytical region arrays on a substrate, for reading in the device. Alternately, the hand held device can be separate from the cartridge, e.g., reading the cartridge by holding the device near the cartridge. The devices can have a user interface to allow selection of features or programming in the field. The devices can include a computer interface, e.g., (preferably wireless, or USB) to download acquired data and/or to upload programming and sample information.

EXAMPLES

The following examples are offered to illustrate, but not to limit the claimed invention.

Example 1

MEMS-Based Handheld Fluorescence Reader for Immunoassay Diagnosis

MEMS (Micro-Electro-Mechanical Systems) is the integration of mechanical elements and electronics on a common silicon substrate. Inherent advantages of MEMS devices are high reliability, low power operation, small size, low cost to manufacture, and high scalability to volume production. These advantages can be utilized to advance a one dimensional (1D) mechanical scanning desktop assay reader into a two dimensional (2D) scanning MEMS-based handheld reader.

MEMS devices have proven their value and reliability in many markets and products, such as, e.g., projection display systems, consumer electronics and medical applications in imaging and blood pressure monitoring. They are also a key element in the highly demanding automotive market's safety restraint system (air bags) and suspension control systems, as well as mobile phone applications such as microphone, resonators and RF switches etc.

Figure 8A:
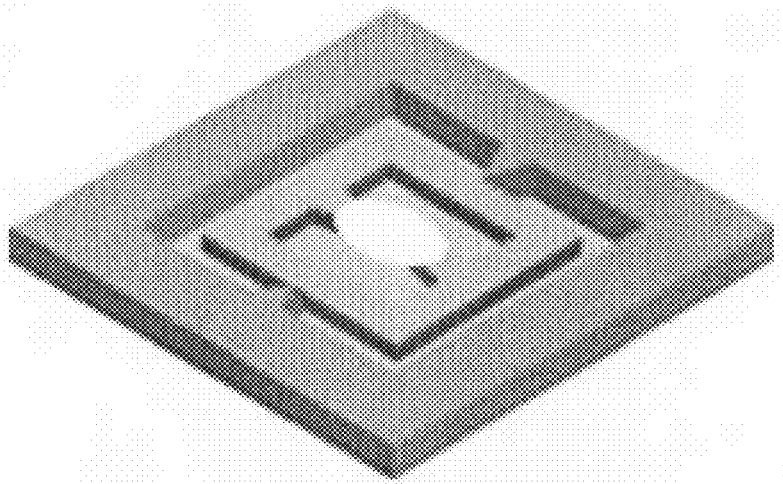
FIGS. 8A to 8C presents exemplary diagrams of digital and scanning micromirrors.
Figure 8B:
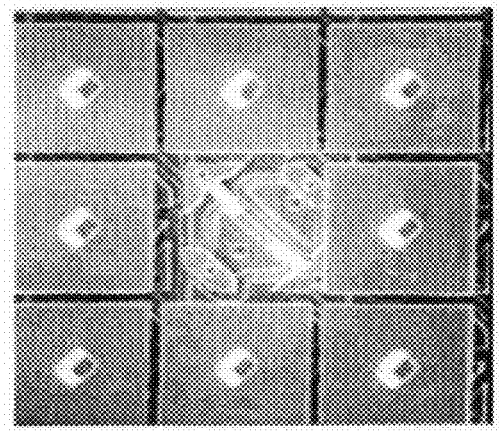
Figure 8C:
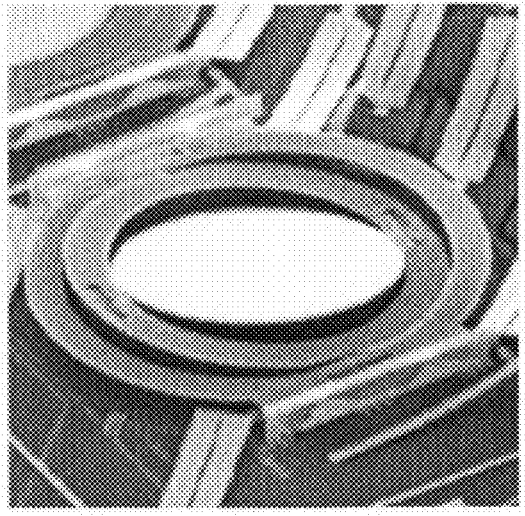

MEMS mirrors can be analogue or digital. Digital mirrors are suited for display matrix applications, while analogue mirrors are suited to scanning mirror applications. FIG. 8 shows typical scanning mirrors used in projection and digital processing applications. The scanning mirror of 8A is a typical scanning mirror used in barcode readers to project a scanning laser beam. The mirror of 8B is a DMD digital mirror with one pivot axis actuated to provide only two optional positions. FIG. 8C is an optical switch mirror with two pivot axes used to direct digital signal transmissions.

Depending on applications and system design, mirror size can be varying from few micrometers to millimeters even centimeters. FIG. 9 demonstrates certain MEMS mirror applications and corresponding mirror size with suitable driving technology.

MEMS scanning mirrors have several advantages for use in handheld assay readers. For example, they provide improved reliability. Due to the low stress degradation characteristics of micro silicon structures, the integrity of the MEMS-engine does not degrade even after millions of scans. The MEMS mirrors are compact and lightweight. The rugged MEMS mirrors are not susceptible to performance degradation resulting from bumps and vibrations often experienced with a handheld device. Other MEMS components can be integrated into a low mass MEMS engine. MEMS micromirrors enable 2D matrix array scanning and multiplexing of assay signals. Semiconductor batch processing for fabricating MEMS devices can enable lower costs of production. MEMS part price can be kept low by utilizing well-established semiconductor processes and producing many devices on a single silicon wafer. As well as being cost effective, these design and manufacturing practices are easily scaled to high volume production.

MEMS processing can employ traditional semiconductor CMOS batch processing techniques for massive scale production of consistent products. Processing can be divided into two categories, e.g., bulk micromachining and surface micromachining. FIG. 10 shows the typical bulk micro-machining by DRIE processing. The advantage of using DRIE bulk micromachining is simple and robust processing with silicon-on-insulator (SOI) or III-V epi wafer, to provide suspended structures in one-step etching and releasing procedures.

Figure 11:
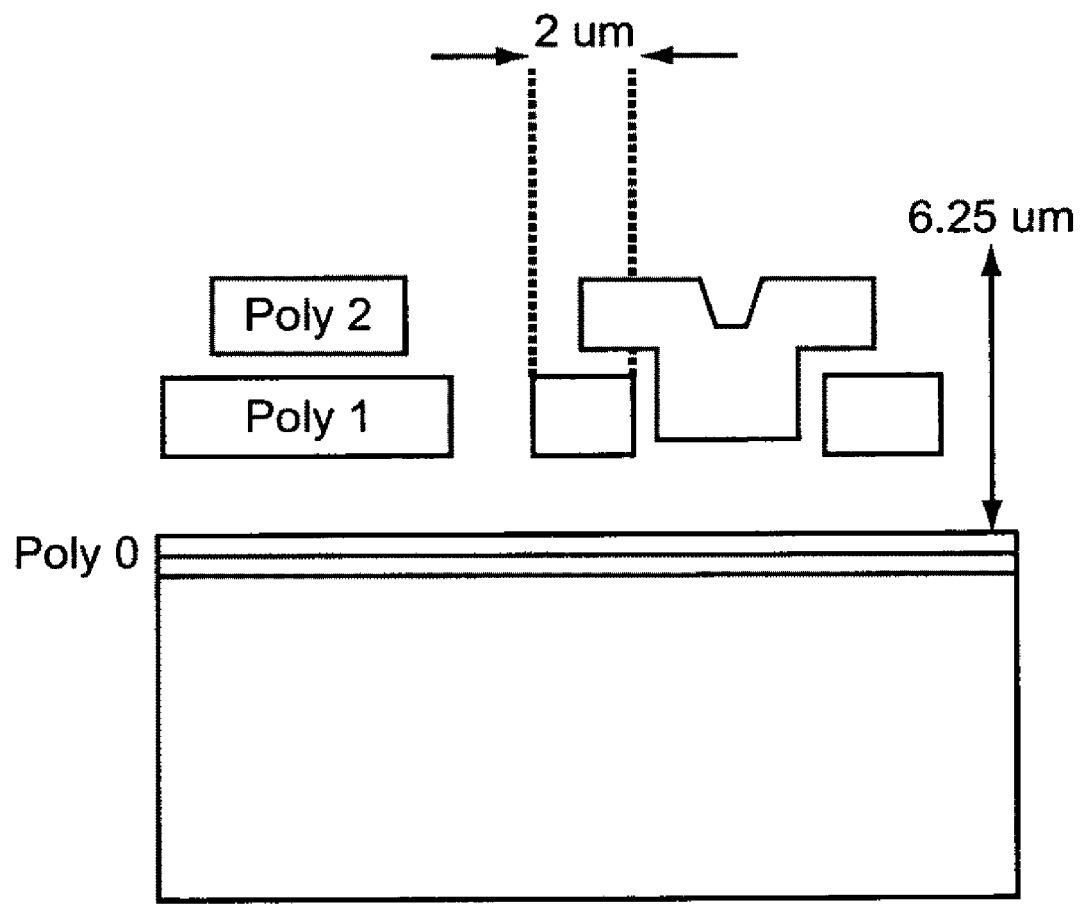
FIG. 11 shows a schematic diagram of MUMPS standardized surface micro-machining.

MEMS foundries have made great efforts to standardize MEMS processing. FIG. 11 is the standard MUMPS surface micromachining processing offered by MEMSCAP.

Figure 12:
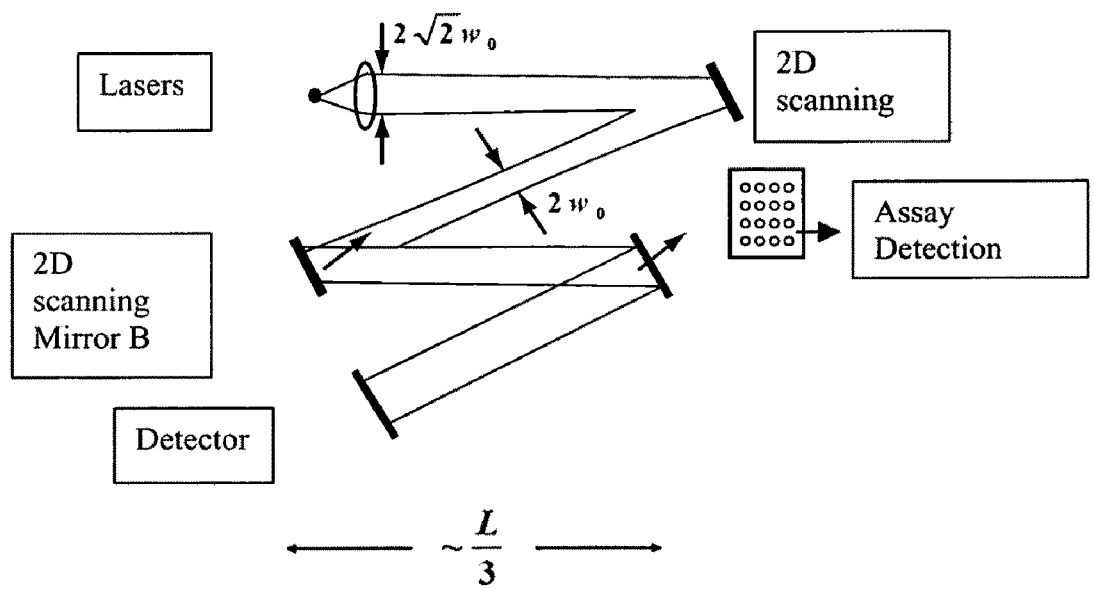
FIG. 12 shows a schematic diagram of a MEMS 2D mirrors assay scanning system.

A schematic diagram of a handheld reader system is provided in FIG. 12. At the heart of the handheld reader is the MEMS-based scanning mirror engine composed of two 2D scanning mirrors between a light source and detector. Interaction of 2 scanning mirrors enables this scanning engine to provide a large scanning field with compact design layout.

Example 2

MEMS Lateral Flow Cartridge Reader

In this MEMS (microelectromechanical systems) mirror scanning based reader, the detection mechanism is based on measuring the reflectivity of detection zones along a lateral flow cartridge. By scanning the detection zones with a MEMS mirror, a concentration of the target analyte chemical can be determined. Potential applications of the reader include medical diagnosis, food safety, and environmental monitoring etc.

Figure 13:
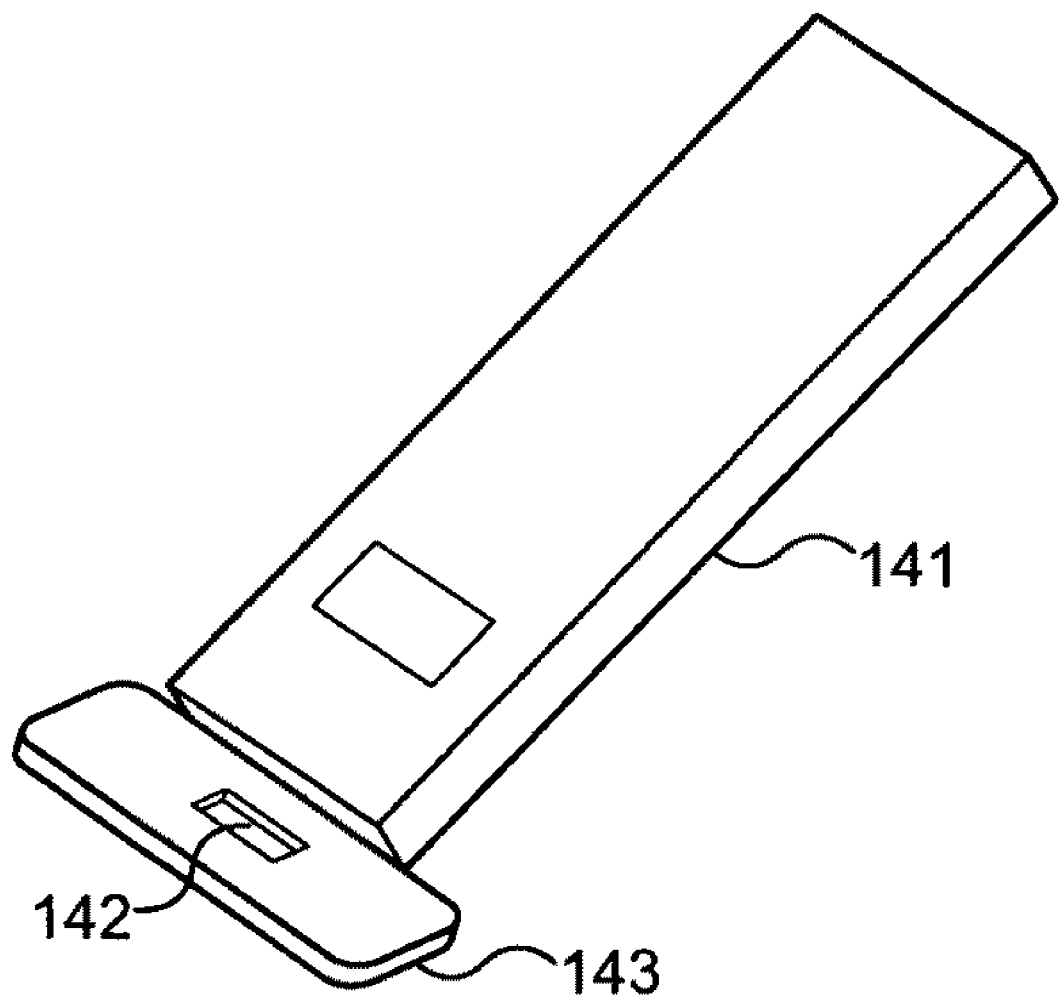
FIG. 13 shows a schematic diagram of a proposed MEMS reader for lateral flow cartridges.
Figure 14:
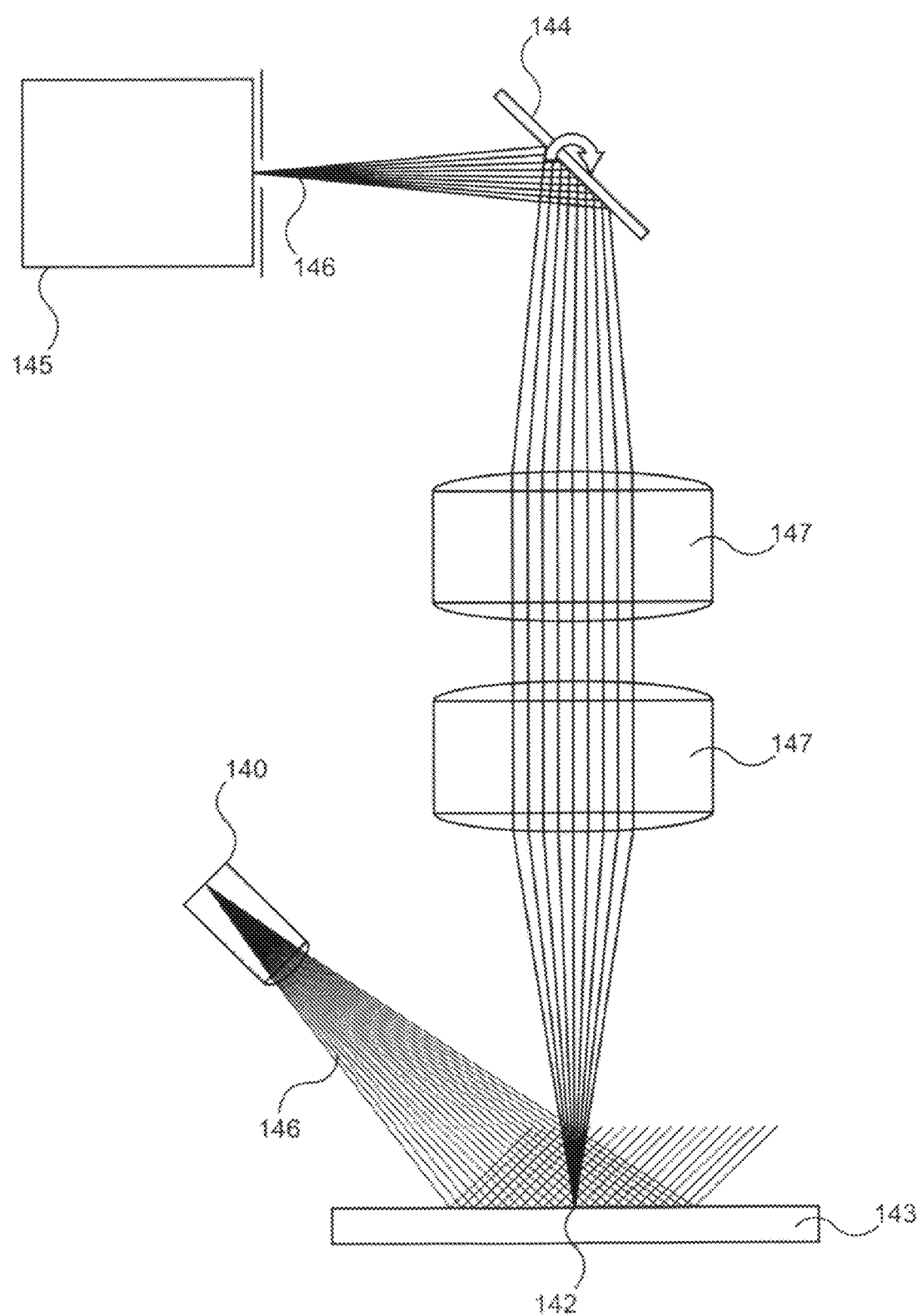
FIG. 14 shows a schematic diagram of a proposed optical layout for a MEMS reader.

The MEMS reader consists of an optical module, a data processing board, and a LCD display as shown in FIGS. 13 and 14. An LED 140 in the optical module 141, is used to illuminate the detection zones 142 of cartridge 143. In order to eliminate interference from ambient light, the LED can be modulated at a frequency that can be discretely detected by a complimentary data processing circuit. Rather than scanning a light beam across the detection zones, image of the detection zone is scanned with a MEMS mirror 144 and projected onto a detector 145 through a slit 146. As the MEMS mirror tilts, light from different detection zones is selectively directed to the detector through the slit. Light reflected, transmitted, fluoresced and/or absorbed at each detection zone can be detected and analyzed. To minimize the background noise at the detector from ambient lighting, the signals can be modulated/encoded at certain frequencies different from ambient lightings, e.g., as discussed above.

The optical layout of the device can be as shown in FIG. 14. Illumination light 146 from LED 140 shines uniformly onto the cartridge detection zone. Light reflected from the cartridge is collected by a pair of lenses 147 and directed onto the MEMS mirror. Because of the limited reception angles through slit 146 in front of the detector 145, the MEMS mirror projects light from only a small area of the cartridge detection zones (e.g., one detection zone) onto the detector at each fixed angle.

The line width of the cartridge is usually in the order or 1 mm. In order to have a sufficient spatial resolution, the slit width should be in the order of 0.1 mm. The MEMS mirror planned for this application is single axis with a scanning angle up to +/−5 degrees.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An analytical device comprising:
   a pivotable mirror comprising two pivot axes;
   a first actuator configured to pivot the mirror on a first of the two axes;
   a second actuator configured to pivot the mirror on a second of the two axes;
   an array of three or more analytical regions, which three regions are not aligned along a straight line; and,
   a light detector oriented to receive light from the mirror;
   wherein the mirror is mounted to pivot on the axes to sequentially reflect light from each of the three regions to the detector.

2. The device of claim 1, wherein the mirror is a micromirror.

3. The device of claim 1, wherein the first or second actuator comprises: an electromagnetic device, an electrostatic device, a thermal actuator or an annular vertical comb actuator.

4. The device of claim 1, wherein the first pivot axis is substantially perpendicular to the second pivot axis.

5. The device of claim 1, wherein the first or second pivot axis is defined by a pivot mount comprising a torsion bar; wherein a pivot angle about the first or second axis depends on the amount of energy applied to the first or second actuator, respectively.

6. The device of claim 1, wherein the analytical regions comprise an array of two or more different reagents or ligands.

7. The device of claim 1, wherein the light received by the detector reflected from the mirror is light selected from the group consisting of: light previously reflected from one of the analytical regions, light transmitted through one of the analytical regions and light fluoresced from one of the analytical regions.

8. The device of claim 7, further comprising a light source directed to illuminate the analytical regions.

9. The device of claim 7, wherein the light received at the detector has not reflected off of any single mirror more than once.

10. The device of claim 1, wherein the mirror and detector are mounted in an analytical cartridge reader and the three analytical regions are on an analytical cartridge.

11. The device of claim 1, wherein the mirror sequentially reflects light from each of the three regions to the detector without relative motion between the detector and the regions.

12. A device comprising:
    a micromirror pivotably mounted at a first pivot axis and at a second pivot axis; and,
    a light detector oriented to receive light reflected directly from the micromirror.

13. The device of claim 12, comprising an actuator associated with the micromirror to provide selectable infinitely variable pivot angles.

14. The device of claim 12, wherein the first or second pivot axis comprises a torsion bar.

15. The device of claim 14, further comprising an actuator configured to twist the torsion bar, whereby variation of force from the actuator varies an angle the micromirror pivots about the axis.

16. The device of claim 12, further comprising one of more actuators configured to pivot the mirror through an angle about the first or second pivot axis.

17. The device of claim 16, wherein pivoting the mirror through the angle reflects light from an analytical region of an analytical cartridge onto the detector.

18. A device comprising:
    two pivotably mounted micromirrors and a light detector or a light source; and,
    a light path from a first of the two micro mirrors to a second of the two micromirrors on to the light detector or light source.

19. The device of claim 18, wherein a pivot axis of a first of the two micromirrors is substantially perpendicular to a pivot axis of the second of the two micromirrors.

20. The device of claim 18, wherein the two micromirrors are fabricated on the same substrate and remain together on the same substrate.

21. The device of claim 18, further comprising:
    one or more actuators configured to pivot the first of the two micromirrors on one or more pivot axis; and,
    one or more actuators configured to pivot the second of the two micromirrors on one or more pivot axis.

22. The device of claim 21, wherein the first or second micromirror comprises a first pivot axis mount and a second pivot axis mount, whereby the first or second micromirror can be pivoted with 2 degrees of freedom.

23. The device of claim 21, wherein the first micromirror and the second micromirror each comprise pivot mounts at two axes, whereby both micromirrors can be pivoted with two degrees of freedom.

24. The device of claim 18, further comprising one or more actuators configured to pivot the first or second micromirror about at least one of the axes.

25. The device of claim 24, wherein the actuators are configured to provide selectable infinitely variable pivoting about the at least one of the axes.

26. The device of claim 18, further comprising: three or more analytical regions not arranged in a straight line; and, wherein the light path runs from one of the regions to the light detector or light source, reflecting off of the first micromirror and off of the second micromirror.

27. A method of detecting assay results on a two dimensional array, the method comprising:
    illuminating one or more analytical regions on the array; and,
    reflecting light from the one or more first analytical regions from a first mirror onto a light detector;
    wherein the first mirror comprises a first pivotable mount defining a first pivotable axis and a second pivotable mount defining a second pivotable axis substantially perpendicular to the first axis.

28. The method of claim 27, wherein light from the one or more analytical regions travels directly from the one or more regions to the mirror.

29. The method of claim 27, further comprising pivoting the mirror on the first axis to reflect light from a second analytical region onto the detector.

30. The method of claim 27, further comprising pivoting the mirror on the second axis to reflect light from a third analytical region onto the detector.

31. The method of claim 27, further comprising reflecting the light off a second mirror between the one or more regions and the detector.

32. A method of scanning light onto a two-dimensional (2D) analytical array, the method comprising:
    directing a beam of light onto a first pivotable mirror comprising a first pivotable axis;
    reflecting the beam of light from the first mirror to a second pivotable mirror having a second pivotable axis not parallel to the first pivotable axis;
    reflecting the beam of light from the second mirror on to illuminate a first analytical region of an array of analytical regions; and,
    pivoting the first mirror on the first axis to redirect the beam to illuminate a second analytical region of the array or pivoting the second mirror on the second axis to redirect the beam to illuminate the second analytical region of the array.

33. The method of claim 32, comprising pivoting both the first mirror and the second mirror to redirect the beam to illuminate the second analytical region of the array.

34. The method of claim 32, comprising pivoting the first mirror or the second mirror on two or more axes to redirect the beam to illuminate the second analytical region of the array.

35. The method of claim 32, further comprising defining the pivotable axes by mounting the first mirror or the second mirror on one or more pivotable mounts.

* * * * *